United States Patent
Kelly et al.

(10) Patent No.: US 6,700,121 B1
(45) Date of Patent: Mar. 2, 2004

(54) METHODS OF SAMPLING SPECIMENS FOR MICROANALYSIS

(75) Inventors: Thomas F. Kelly, Madison, WI (US); Richard L. Martens, Madison, WI (US); Steven L. Goodman, Madison, WI (US)

(73) Assignee: Imago Scientific Instruments, Madison, WI (US)

( * ) Notice: Subject to any disclaimer, the term of this patent is extended or adjusted under 35 U.S.C. 154(b) by 28 days.

(21) Appl. No.: 10/428,372

(22) Filed: May 1, 2003

Related U.S. Application Data

(63) Continuation of application No. 09/861,405, filed on May 18, 2001, now Pat. No. 6,576,900.
(60) Provisional application No. 60/205,456, filed on May 19, 2000.

(51) Int. Cl.⁷ ................................................. G01N 1/32
(52) U.S. Cl. ........................... 250/307; 250/304; 216/2; 438/14
(58) Field of Search ................................ 250/307, 304; 216/2; 438/14

(56) References Cited

U.S. PATENT DOCUMENTS

| | | | |
|---|---|---|---|
| 4,060,440 A | 11/1977 | Behme et al. | |
| 4,066,728 A | 1/1978 | Behme et al. | |

(List continued on next page.)

FOREIGN PATENT DOCUMENTS

| | | | | |
|---|---|---|---|---|
| DE | 197 55 990 C1 | 3/1999 | | |
| EP | 0 784 211 A2 | 7/1997 | | |
| JP | 7-43373 | 2/1995 | | |
| JP | 2001208659 A | * 8/2001 | ............ | G01N/1/28 |

OTHER PUBLICATIONS

Nishikawa, O. and Kimoto, M., Toward a scanning atom probe–computer simulation of electric field, Appl. Surf. Sci. 76/77:424–430 (1994).

Nishikawa, O., Kimoto, M., and Ishikawa, Y., Development of a scanning atom probe, J. Vac. Sci. Technol. B, 13:599–602 (1995).

Nishikawa, O., Ohtani, Y., Meada, K., Watanabe, M., and Tanaka, K., "Development of the Scanning Atom Probe and Atomic Level Analysis," Materials Characterization, vol. 44 (2000) pp. 29–58.

Kelly, T.F., Camus, P.P., Larson, D.J., Holzman, L.M. and Bajikar, S.S., On the many advantages of local electrode atom probes, Ultramicroscopy 62:29–42 (1996).

(List continued on next page.)

*Primary Examiner*—Jack Berman
(74) *Attorney, Agent, or Firm*—Craig A. Fieschko, Esq.; DeWitt Ross & Stevens S.C.

(57) ABSTRACT

Methods of sampling specimens for microanalysis, particularly microanalysis by atom probe microscopy, include steps of forming a study specimen in a first study object (as by use of focused ion beam milling); removing the study specimen from the study object; situating the study specimen on a second study object; and microanalyzing the study specimen. Where the first study object is of particular interest for study, the study specimen may be taken from a functional portion of the first study object so that microanalysis will provide information regarding this functional portion. Where the second study object is of particular interest for study, the second study object may be subjected to manufacturing processes (e.g., deposition of layers of materials) after the study specimen is situated thereon so that the study specimen will provide information regarding the results of the manufacturing process. The study specimen may have study regions formed thereon which are particularly suitable for study by atom probes, e.g., regions bearing raised protrusions, at virtually any point during the process, thereby greatly enhancing the speed and efficiency of specimen preparation.

23 Claims, 4 Drawing Sheets

U.S. PATENT DOCUMENTS

| | | |
|---|---|---|
| 4,128,765 A | 12/1978 | Franks |
| 4,340,815 A | 7/1982 | Franks |
| 4,939,364 A | 7/1990 | Ishitani et al. |
| 5,009,743 A | 4/1991 | Swann |
| 5,061,850 A | 10/1991 | Kelly et al. |
| 5,214,282 A | 5/1993 | Yamaguchhi et al. |
| 5,270,552 A | 12/1993 | Ohnishi et al. |
| 5,333,495 A | 8/1994 | Yamaguchi et al. |
| 5,440,124 A | 8/1995 | Kelly et al. |
| 5,563,412 A | 10/1996 | Zandbergen et al. |
| 5,619,035 A | 4/1997 | Weiss et al. |
| 5,621,211 A | 4/1997 | Spence |
| 5,656,811 A | 8/1997 | Itoh et al. |
| 5,764,409 A | 6/1998 | Colvin |
| 5,788,853 A | 8/1998 | Zenhausern |
| 5,922,179 A | 7/1999 | Mitro et al. |
| 5,926,688 A | 7/1999 | Lee et al. |
| 5,935,870 A | 8/1999 | Lee |
| 5,986,264 A | 11/1999 | Grünewald |
| 5,990,478 A | 11/1999 | Liu |
| 5,993,291 A | 11/1999 | Tsai et al. |
| 6,042,736 A | 3/2000 | Chung |
| 6,060,707 A | 5/2000 | Fujihara |
| 6,080,991 A | 6/2000 | Tsai |
| 6,140,603 A | 10/2000 | Hwang et al. |
| 6,140,652 A | 10/2000 | Shlepr et al. |
| 6,188,068 B1 | 2/2001 | Shaapur et al. |
| 6,188,072 B1 | 2/2001 | Chung |
| 6,194,720 B1 | 2/2001 | Li et al. |
| 6,576,900 B2 * | 6/2003 | Kelly et al. .......... 250/307 |

OTHER PUBLICATIONS

Kelly, T.F. and Larson, D.J., "Local Electrode Atom Probes," (Invited review) Materials Characterization, vol. 44 (2000) pp. 59–85.

Giannuzzi, L.A., "A Tutorial of the FIB Lift–out Technique for TEM Specimen Preparation," Microac. Microanal. 5 (Suppl. 2: Proceedings), Springer Verlag (1999) pp. 516–517.

Sheng, T.T., Goh, G.P., Tung, C.H., and Wang, L.F., "Precision transmission electron microscopy sample preparation using a focused ion beam by extraction method," Journal of Vacuum Technology B, May/Jun. 1997.

International Search Report for PCT/US01/16185.

* cited by examiner

METHODS OF SAMPLING SPECIMENS FOR MICROANALYSIS

CROSS-REFERENCE TO RELATED APPLICATIONS

This application is a continuation claiming priority under 35 USC §120 to U.S. patent application Ser. No. 09/861,405 filed May 18, 2001, now U.S. Pat. No. 6,576,900 which in turn claims the benefit under 35 USC §119(e) of U.S. Provisional Patent Application No. 60/205,456 filed May 19, 2000. The entireties of these applications are incorporated by reference herein.

FIELD OF THE INVENTION

This disclosure concerns an invention relating generally to methods for obtaining and preparing specimens for microscopic analysis, and more specifically to methods of obtaining and preparing specimens for micron-scale and sub-micron-scale analysis, particularly specimens of multilayered materials, and materials upon which thin films have been deposited, implanted or otherwise incorporated (e.g., semiconductor wafers, photonic devices).

BACKGROUND OF THE INVENTION

In the manufacture of many modern devices containing microscopically thin layers of different materials, and/or zones of different materials segregated on a microscopic scale, it is important to be able to study the different layers and/or zones with analytical equipment after the deposition. As examples, it is often useful to be able to microscopically analyze the structures of semiconductor microelectronic devices; magnetic thin film memory storage devices (such as read/write hard disk heads and platters); thin film based optical devices; multilayered polymeric, organic and/or biochemical based thin film devices (as used in medicine); composites of inorganic materials, organic materials and/or biological materials (such as bioMEMs, biosensors, bioarray chips, and integrated labs on chips); and other devices wherein nanoscale structures are critical to device function. Common equipment used for such analysis (hereinafter referred to as "microanalysis") includes electron microscopes (including TEMs, Transmission Electron Microscopes, and SEMs, Scanning Electron Microscopes); spectrometers (including Raman spectrometers and Auger spectrometers); photoelectron spectrometry (XPS); Secondary Ion Mass Spectrometry (SIMS); and more recently, the atom probe microscope, as described in U.S. Pat. Nos. 5,061,850 and 5,440,124. Of course, other microanalysis equipment is available, and new equipment having different principles of operation is expected to become available over time.

Generally, microanalysis of an entire device is not feasible owing to practical constraints, and thus specimens of portions of the device are studied. Ideally, the specimen of the device under study is formed from the actual material that is intended to perform a function in the device. Accordingly, destructive testing methods are known wherein study specimens are "biopsied" from the objects being studied, and are then subjected to microanalysis. As an example, Focused Ion Beam (FIB) milling processes are often used to excise study specimens from study objects. A good background discussion of FIB processes is set forth in U.S. Pat. No. 6,042,736 to Chung. U.S. Pat. No. 6,188,072 is then of interest for its discussion of a method (allegedly described by the FEI Company of Hillsboro, Oreg. USA) of cutting a study specimen from a study object by FIB milling, with the study specimen then being removed by a micromanipulator by use of electrostatic attraction. The study specimen is then subjected to TEM microanalysis. The remainder of the patent is directed to a micromanipulator suitable for performing this operation. U.S. Pat. No. 6,188,068 to Shaapur et al. appears to describe a similar method, and the Background section of U.S. Pat. No. 5,270,552 also appears to describe similar methods for preparing study specimens using FIB milling and mechanical cutting/polishing steps.

U.S. Pat. No. 6,194,720 to Li et al. describes a method wherein a study object is milled by FIB and other processes to produce a thin cross-sectional study specimen suitable for microanalysis by a TEM. One aspect of the method involves milling a pair of parallel trenches in the top surface of the study object to define a plate-like first study region therebetween (FIGS. 2A–2C of Li et al.), and then filling in the trenches with filler material (FIG. 2D). Portions of the study object are then cut away along planes parallel to the first study region and intersecting the filled trenches (FIG. 3B), or being spaced a short distance away from the filled trenches (FIG. 3C). As a result, the study object is formed into a plate-like shape wherein the first study region defines an area of decreased thickness. The plate-like study object is then milled into a wedge-like form (FIGS. 4A and 4B) wherein the thinner side(s) of the study object define a second study region. The first and second study regions thereby define thin plate-like areas on the study object wherein the various deposited layers of the study object are displayed. A somewhat similar arrangement is described in U.S. Pat. No. 5,656,811, which is more directly devoted to methods of controlling the FIB milling process.

U.S. Pat. No. 5,270,552 describes a process wherein a study specimen is partially severed from a study object using FIB milling (with the study specimen remaining attached to the study object by a thin bridge of material), a probe is then connected to the partially-disconnected study specimen (as by "soldering" it thereon with FIB deposition), and then the study specimen is fully removed by cutting away the bridge with FIB milling so that the probe may carry the study specimen to a desired location for study. By using an electrically conductive probe, the voltage between the probe, study specimen, and bridge can provide a measure of whether the study specimen is intact. The probe may also serve as a support structure for further preparation of the study specimen, or for use during the study specimen's microanalysis. Use of the process to obtain multiple study specimens from points spaced about a semiconductor wafer is illustrated. The patent additionally discusses the use of the underlying process steps to separate elements from one chip, transport them to another chip by use of the probe, and then sever the probe and "solder" the elements to the second chip by use of FIB deposition.

Other patents note that study specimens can be formed from a study object by use of material removal processes other than FIB processes (and any accompanying polishing or other mechanical material removal processes). U.S. Pat. No. 6,140,652 to Shlepr et al. describes the formation of study specimens from a study object for TEM microanalysis using photolithography and chemical etching processes. Trenches are etched in the study object to form a circular plug-like study specimen, which then has its base cut free from the study object by further chemical etching techniques. The study specimen can then be microanalyzed using TEM techniques.

In many instances, destructive testing (as in the foregoing methods) is undesirable because it will effectively render the study object inoperable. Thus, in some cases "proxy" or "qualifier" study objects are used: objects which are not the true study objects of interest, but which are subjected to the same processes so that they (hopefully) serve as a reasonable representation of the product generated by these processes. As an example, in the field of semiconductors, many thin film deposition systems are designed to deposit layers over an area greater than the size of a typical semiconductor wafer. Qualifier wafers are often processed alongside actual wafers so that they receive the same deposited layers as the production wafer. The qualifier wafer is then destructively tested in place of the actual wafer. However, testing of a qualifier wafer assumes that the qualifier wafer receives the same treatment as the actual wafer within the deposition system, an assumption which is not always valid because the deposited coatings may vary in time or location within the deposition system.

One significant problem encountered with all known methods is the time and expense of subsequent testing. Often, individual study specimens, once obtained in accordance with the foregoing methods, must then be individually prepared for subsequent microanalysis. This can include steps such as polishing, mounting, application of protective or other layers, situating the study specimen in a vacuum environment, and so on. Because of the disadvantages of destructive test methods, and because of the time and expense involved in the microanalysis of individual study specimens, there is a need for new methods of microanalysis which are nondestructive (or at least minimally destructive), and which are better suited for rapid processing of multiple study specimens.

SUMMARY OF THE INVENTION

The invention involves methods which are intended to at least partially solve the aforementioned problems. To give the reader a basic understanding of some of the advantageous features of the invention, following is a brief summary of preferred versions of the methods. As this is merely a summary, it should be understood that more details regarding the preferred versions may be found in the Detailed Description set forth elsewhere in this document. The claims set forth at the end of this document then define the various versions of the invention in which exclusive rights are secured.

The invention includes methods of obtaining and preparing specimens, particularly specimens of thin film materials and other materials having distinct zones of different materials arrayed on a micron or sub-micron scale (e.g., integrated circuit wafers), for study by microanalysis equipment. The invention is particularly suitable for preparing specimens for microanalysis with an atom probe, which is a preferred mode of microanalysis because it can produce three-dimensional compositional images with atomic-scale resolution. This capability of atom probes is especially attractive for studying and characterizing the small-scale structures typically found in microelectronic devices that are used, for example, in integrated electronic circuits and the read/write heads of data storage devices. Historically, atom probes have utilized a needle-shaped study specimen (or a study specimen having a needle-shaped study region formed thereon), since such a needle shape is beneficial for creating the high electric fields required for atom probe microanalysis. Where the study specimen or study region is wire-shaped, this shape readily lends itself to needle creation; otherwise, the region to be studied must be cut into a suitable needle-like shape, as by FIB milling. Planar structures like wafer-processed materials, e.g., microelectronic materials, are often difficult to cut into atom probe specimens because the structures of interest exist only in a very thin layer on the surface of the specimen that is often less than about 10 micrometers (microns) thick. However, with advances in atom probe technology, and with the advent of scanning atom probes and local electrode atom probes, it is possible to use atom probes to microanalyze specimens that are raised in relation to their surroundings by as little as a few micrometers, and which are closely spaced (e.g., by no more than a few micrometers away) in relation to adjacent protrusions. For example, local electron atom probes only require a small protrusion on the specimen (a few microns high) for the local electrode to be able to locally apply the necessary extraction field to the specimen in order to effect ionization.

In a first preferred version of the invention, a study specimen is formed from a larger first study object such as an integrated circuit wafer, as by cutting the study specimen therefrom by the use of FIB milling. The study specimen will generally be a portion of the first study object item which is of key interest for microanalysis, e.g., a functional section of a semiconductor chip. The study specimen is then removed from the first study object, and is situated on a second study object such as a silicon-based wafer whereupon the study specimen is microanalyzed. Preferably, the study specimen (and perhaps several other study specimens) are also inserted within recesses in the second study object, and/or are affixed to the second study object (as by FIB deposition). The study specimen(s) can then be microanalyzed on the second study object, which can be constructed and configured to enhance the speed and ease of microanalysis; for example, the second study object may be formed of a material which promotes electrostatic attraction of the study specimen to the second study object (either by itself or with the assistance of an applied charge), thereby assisting in the placement of the study specimen on the second study object.

In a second preferred version of the invention, a study specimen is formed from a larger first study object such as a silicon-based wafer, as by cutting the study specimen therefrom by use of FIB milling. The study specimen is removed from the first study object and is situated on a second study object, with the second study object in this case generally being the item of primary interest for microanalysis rather than the first study object. The study specimen (and perhaps multiple other study specimens) can additionally be inserted within recesses formed in the second study object, and/or can be affixed to the second study object (as by FIB deposition). Where the study specimen is recessed within the second study object, it is often also useful to render the study specimen at least substantially coplanar with the second study specimen, as by the use of polishing processes. The second study object (with the study specimen thereon) is then subjected to any desired manufacturing processes, e.g., layer deposition processes, so that the study specimen and second study object both reflect the results of such processes. The study specimen may then be microanalyzed for desired information regarding the effects of the manufacturing process, preferably after removal from the second study object. Here, the second study object (and more specifically the effect of the manufacturing process on the second study object) is of primary interest for microanalysis, but the study specimen is analyzed in place of the second study object so that the second study object may be left intact, without the need to excise a portion of the second study object (as is done to the first study object in the first version of the invention). During the foregoing process, the study specimen is preferably placed on a nonfunctional portion of the second study object so that the study specimen does not interfere with the effects of the manufacturing process on the second study object; for example, where the second study object is a semiconductor chip bearing an integrated circuit, the study specimen is preferably placed on a portion of the chip which does not bear the circuit so that the circuit emerges from the manufacturing process in an operable state.

Where an atom probe is used for microanalysis of the study specimens, it will generally be useful to form study regions on the study specimens wherein protrusions are defined for generation of the desired extraction voltage. The study regions (and the protrusions therein) may be formed in the study specimens at the outset of the foregoing methods (e.g., when the study specimens are first formed), or near the end of the foregoing methods (e.g., immediately prior to microanalysis). Formation of the study regions during construction of the study specimens themselves is particularly preferred for sake of speed and efficiency, and methods are described later in this document for allowing such early formation of the study regions without leading to significant degradation in the quality of data obtained during later microanalysis.

The invention is particularly well adapted to allow sampling of objects for microanalysis while the objects are being manufactured, with minimal or no damage to the object being sampled, and with exceptionally rapid preparation of specimens for microanalysis. Further advantages, features, and objects of the invention will be apparent from the following detailed description of the invention in conjunction with the associated drawings.

DETAILED DESCRIPTION OF PREFERRED EMBODIMENTS OF THE INVENTION

In a first version of the invention, a study specimen is formed from a larger study object, such as a semiconductor wafer of interest, using methodologies similar to those previously described for TEM specimen preparation. The study specimen is then situated on a second study object which effectively serves as a specimen holder. The study specimen is microanalyzed while resting on the specimen holder, preferably by an atom probe after the study specimen has had study regions formed thereon (e.g., raised study regions) which are well-suited for atom probe microanalysis. A more detailed description follows.

Figure 1:
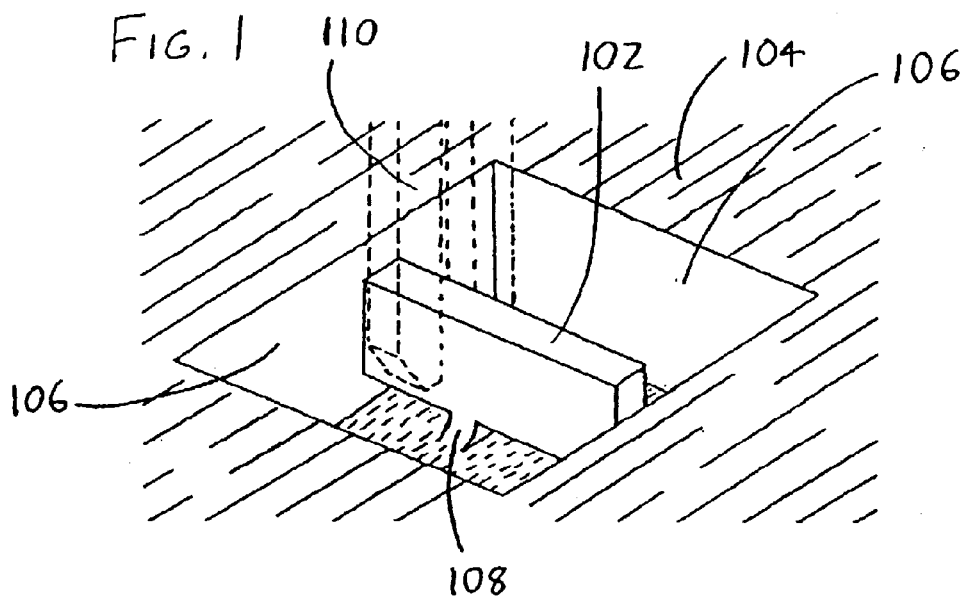
FIG. 1 is a top perspective view of a study specimen 102 formed in a first study object 104 prior to its removal therefrom (with a micromanipulator 110 suitable for such removal being shown in phantom).

Initially, a study specimen is formed in a larger study object of interest, such as a semiconductor wafer. Once the area of interest on the study object is identified as the area from which the study specimen is to be obtained, a study specimen can be formed in the study object at this area using known cutting techniques such as FIB milling, etching, and so forth. An example is illustrated in FIG. 1, wherein a study specimen 102 is formed in a surface 104 of a study object by using FIB milling to form two adjacent parallel trenches 106 in the study object surface 104; joining the trenches 106 at their ends so that the study specimen 102 is defined by a freestanding cantilevered wall; and then milling away a portion of the base of the wall so that the study specimen 102 is connected to the study object 104 by a small tether 108.

The study specimen 102 may then be broken from the study object 104 at its tether 108, and the study specimen 102 may be removed from the study object 104 by use of a micromanipulator (such as the ones described in U.S. Pat. No. 6,188,072 and elsewhere). A pincers-like micromanipulator having opposable jaws 110 is illustrated in FIG. 1, and by grasping the study specimen between the jaws 110 while tilting the study specimen 102 into another plane, the tether 108 may be broken so that the study specimen 102 can be easily removed.

Figure 2:
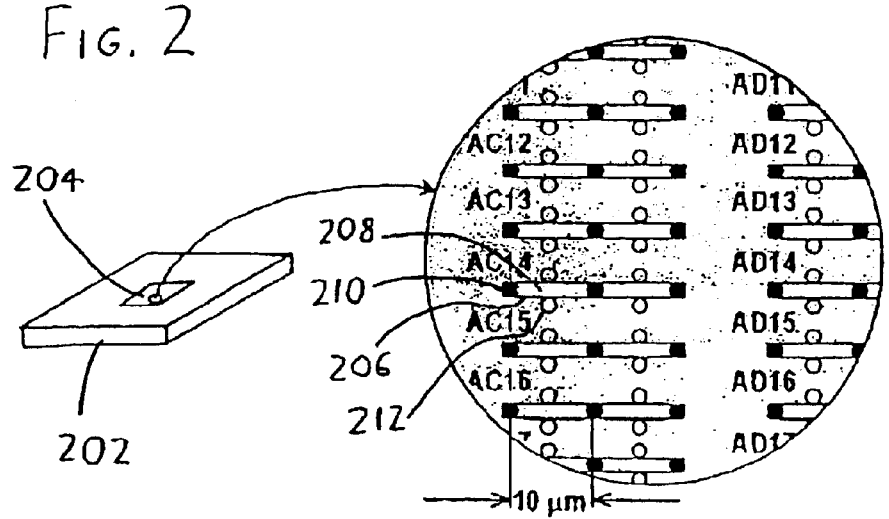
FIG. 2 is a top perspective view of a second study object 202 which serves as a specimen holder wherein a study specimen similar to that of FIG. 1 is placed during microanalysis, with an enlarged view of the second study object 202 being shown wherein numerous study specimens 208 are inserted.

The study specimen 102 is then placed on a second study object which serves as a specimen holder during later microanalysis. Most preferably, the second study object includes a number of recesses whereby the study specimen 102 may be placed in a desired recess, and additional study specimens may be placed in other recesses, so that the second study object may be situated in an atom probe apparatus or other microanalyzer so that some or all of the various study specimens 102 may be sequentially or simultaneously microanalyzed. FIG. 2 illustrates an exemplary second study object 202 having a central storage area 204 wherein several recesses 206 are formed, with each site being marked, or the sites being logically arrayed, so that study specimens 208 placed within the recesses 206 may be more easily correlated with their recesses 206 (thereby allowing for easier later identification of the placed study specimens 208). The recesses 206, as well as any associated markings, may be formed in the second study object 202 by various processes such as FIB milling, deep etching, and/or electroforming. The recesses 206 preferably extend through only a part of the thickness of the second study object 202 rather than through its entire thickness. It should be understood that any storage area 204 wherein study specimens 208 are stored need not be situated in a central location on the second study object 202, nor need it have boundaries which are complementary to the boundaries of the second study object 202, as shown in FIG. 2; rather, the recesses 206 may be arrayed to define storage areas 204 of any size or shape, or multiple storage areas 204 which each contain a discrete set of recesses 206 can be defined and arranged as desired on a second study object 202. Where the second study object 202 is a standard 6-inch diameter silicon wafer, approximately 1600 recesses 206 can be formed in the second study object 202 wherein study specimens 208 having dimensions of approximately 20 micrometers long and 2 micrometers wide may be stored. FIG. 2 illustrates study specimens 208 having these dimensions which have been processed to each bear three study regions 210 suitable for microanalysis by an atom probe, as by milling away adjacent areas of the study specimens 208 so that the study regions 210 remain as rod-like raised protrusions. Such milling could occur after the study specimens 208 are received within their respective recesses 206, or it could instead be performed beforehand, e.g., during the initial formation of each study specimen 208 from its first study object.

The second study object 202 is preferably made of a material which promotes electrostatic attraction between a study specimen 208 and the second study object 202, and/or which may be charged to selectively attract or repel the study specimen 208 as desired. As an example, where a study specimen 208 is extracted from a semiconductor wafer, the second study object 202 may be constructed from a silicon wafer or from copper. Thus, if desired, a voltage may be applied to the second study object 202 so that the study specimen 208 is electrostatically attracted to the surface of the second study object 202 and to a recess 206 therein. If the recesses 206 extend through the entire thickness of the second study object 202 so as to effectively define passages therein, it is also possible to situate material beneath the second study object 202 which is well-suited for generation and/or storage of an electrostatic charge, whereas the second study object 202 might not itself be well-suited for such generation and/or storage. In this case, the electrostatic attraction to the study specimen 208 can be effectively isolated to the recesses 206.

After the study specimens 208 are placed in or on the second study object 202, the second study object 202 can be readied for use in an atom probe by affixing the study specimens 208 to the second study object 202, as by using FIB deposition of a metal, or by applying an adhesive or solder, at the boundaries where the study specimens 208 abut the second study object 202 (or by affixing the study specimens 208 to the second study object 202 at areas which are preferably located away from the study regions 210, e.g., by affixing the regions situated between the study regions 210 to the second study object 202 at the areas labeled 212). Where microanalysis is to be performed by other than an atom probe, other types of final preparation prior to microanalysis can be performed (e.g., deposition of protective layers, polishing, etc.). The second study object 202, and any study specimens 208 provided thereon or therein, may then be placed in an atom probe or other microanalyzer so that selected study specimens 208 may be microanalyzed.

In this first preferred version of the invention, study specimens are taken from a first study object of interest (wherein the first study object has usually already been subjected to processing, e.g., to layer deposition methods), and the study specimens are placed on a second study object for microanalysis (with the second study object perhaps being chosen to have desired material properties which enhance the speed and ease of microanalysis, but wherein the second study object is usually not of direct interest for study). A second preferred version of the invention follows similar steps, but in a sense can be said to represent a situation where the first and second study objects exchange roles. In this second version, the study specimens are taken from a first study object which may be chosen to have desired material properties (but wherein the first study object is usually not of direct interest for study itself), and the study specimens are placed on a second study object which is subjected to layer deposition or other manufacturing processes. The study specimen (and more particularly its deposited layers) is then microanalyzed, preferably by an atom probe after the study specimen has had regions formed thereon (e.g., raised study regions) which are well-suited for atom probe microanalysis. The study specimens may then be microanalyzed on the second study object, or more preferably after removal from the second study object. In effect, the study specimens serve as proxy or qualifier specimens which are associated with and subjected to the same processes as the second study object, and can therefore be studied in lieu of the second study object to serve as its proxy and avoid destructive testing of the second study object (though the study specimens may themselves be destructively tested). A more detailed description follows.

Figure 3:
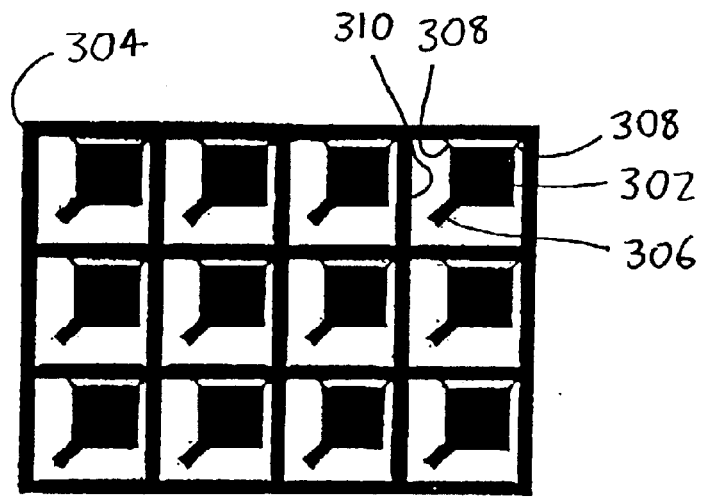
FIG. 3 is a top plan view of several study specimens 302 formed from a first study object 304 (or a portion thereof), with the study specimens being suitable for removal and later microanalysis.

Initially, one or more study specimens are formed in a first study object. This can be done by milling or otherwise forming the study specimens from the first study object in the manner previously described with reference to FIG. 1, but it is also possible to form study specimens from the first study object in bulk. This scheme is illustrated in FIG. 3, wherein an exemplary set of study specimens 302 is shown affixed within a specimen matrix 304 formed from a first study object, such as a thin silicon wafer or other material which is etched or otherwise processed to generate the specimen matrix 304. Regarding silicon study specimens 302, suitable wafer "blanks" for creation of the specimen matrix 304 are available from Virginia Semiconductor, Fredericksburg, Va. (USA). The study specimens 302, which include protruding handles 306, are connected by thin tethers 308 to the framework 310 of the specimen matrix 304. Thus, when a handle 306 or other portion of a study specimen 302 is sped by a micromanipulator (such as the one illustrated in phantom in FIG. 1), its study specimen 302 may be tipped out of the plane of the matrix framework 310 to break its tethers 308 and allow the study specimen 302 to be removed. By repeating a specimen matrix pattern such as the one shown in FIG. 3, an arbitrarily sized wafer can be made to include a very large number of study specimens 302.

Figure 4:
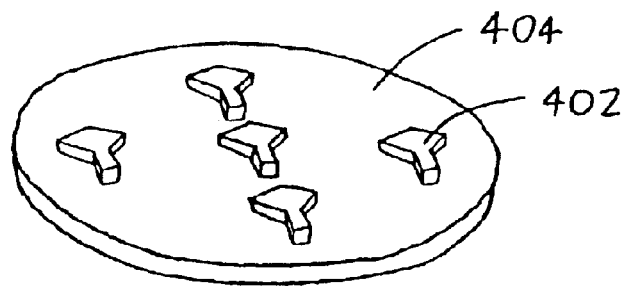
FIG. 4 is a top perspective view of a second study object 404 which is to be subjected to layer deposition or other manufacturing processes, and which has study specimens 402 similar to those of FIG. 3 placed thereon prior to such processes so that the study specimens 402 can later be removed to study the effects of such processes.

Referring then to FIG. 4, after a study specimen 302 is removed from the first study object (and from its specimen matrix 304, if present), it may be situated by the micromanipulator on a second study object as depicted at 404. The second study object 404 is in this version of the invention the study object of key interest, and is illustrated as a silicon wafer which has not yet undergone some or all of its processing steps (e.g., all material layers have not yet been deposited). FIG. 4 illustrates five study specimens 402 situated on the second study object 404, with the intent being that the study specimens 402 will accompany the second study object through some or all of its subsequent processing steps so that they receive the same treatment as the second study object 404. Thus, when the study specimens 402 are subsequently microanalyzed, they should reveal information regarding the processing of the second study object 404 without requiring that the second study object 404 be destructively tested. It should be understood that the study specimens 302 shown on the second study object 402 are not shown to scale, and they would generally be much smaller with respect to the second study object 402. Additionally, it should be understood that more or fewer than five study specimens 302 can be placed on the second study object 402, though the five-point placement of FIG. 4 will often be sufficient because it allows testing of parameters along two directions with three test points in each direction. Also, since it will generally be desirable to have the second study object 404 emerge from processing as a complete and operable article of manufacture, it should be understood that the study specimens 402 are preferably situated on the second study object 404 in nonfunctional blank or "dead" locations on the second study object 404 so that their presence does not interfere with processing of the second study object 404 in critical functional locations.

It will often be useful to choose materials for the study specimens 402 such that they have generally the same adhesion and other characteristics as the second study object 404 when layers are deposited, and/or the second study object 404 is subjected to other manufacturing processes, so that the study specimens 402 will accurately represent the second study object 404 after processing. For example, when the second study object 404 is a semiconductor chip, which is primarily composed of silicon, a silicon study specimen 402 is recommended for use to provide a proxy which will demonstrate substantially the same level of layer adhesion as the second study object 404. It is also useful to choose materials for the study specimens 402 such that they demonstrate some degree of adhesion to the second study object 404 via electrostatic attraction, and/or so that they can be made to exhibit such adhesion when a charge is applied to the second study object 404. Taking again the example of a second study object 404 which is primarily composed of silicon, a silicon study specimen 402 is recommended because it will directly and strongly adhere to the second study object 404, and such study specimens 402 can be can be made to stick or release to the second study object 404 by applied voltage. The ability to promote adhesion and removal of the study specimens 402 by the second study object 404 and/or by micromanipulators facilitates automation of the process. The affixment mechanism between the study specimens 402 and the second study object 404 could be by means other than (or means additional to) electrostatic attraction, for example, by magnetic forces, application of solders or polymeric adhesives, or other forms of attachment. However, it is desirable that any mode of affixment used be easily reversible in order to facilitate the removal of the study specimens 402, and any adhesive (if one is used) should not significantly interfere with the treatment of the study specimens 402 during the manufacturing process (i.e., the study specimens 402 should accurately receive and reflect the effects of the manufacturing process).

Figure 5:
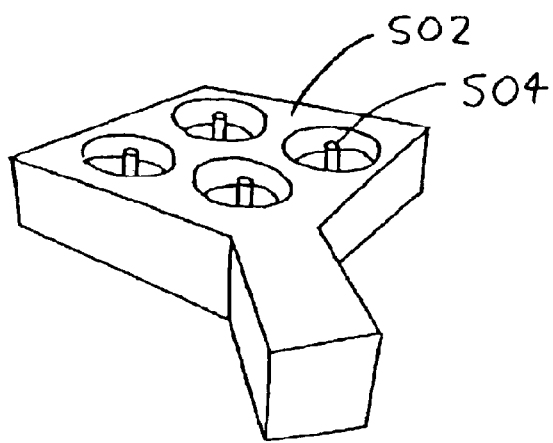
FIG. 5 is a top perspective view of a study specimen 502 similar to those of FIGS. 3 and 4, wherein four study regions 504 suitable for microanalysis in an atom probe have been defined.

After the second study object 404 has undergone some or all processing steps, one or more selected study specimens 402 can be microanalyzed by one of the aforementioned microanalysis tools (or others), either while resting on the second study object 404 or after being removed therefrom. Removal can occur by use of the aforementioned micromanipulators, and where atom probe microanalysis is to occur, study regions (e.g., raised "hills" or rods) may be formed on the removed study specimen(s) 402 prior to microanalysis. FIG. 5 illustrates a study specimen 502 wherein four study regions 504 suitable for atom probe microanalysis have been formed by FIB milling or other etching methods. It should be understood that more or fewer study regions may be formed on a study specimen as desired, and as dictated by the size of the study specimen and the level of detail achievable by the etching method being used.

In a third preferred version of the invention not explicitly shown in the accompanying drawings, the placement of multiple study specimens 402 on the second study object 404 is simplified by taking a specimen matrix bearing multiple study specimens 402, such as the specimen matrix 304 of FIG. 3, and placing the entire specimen matrix on the second study object. The framework of the matrix (i.e., the part of the matrix apart from the study specimens) may then be adhered to the second study object so that any one or more study specimens 402 are easily removable from the framework and the second study object by breaking them off at the tethers connecting them to the framework. The second study object may then undergo processing, and any of the desired study specimens 402 may be microanalyzed on the second study object or after being removed therefrom.

Figure 6:
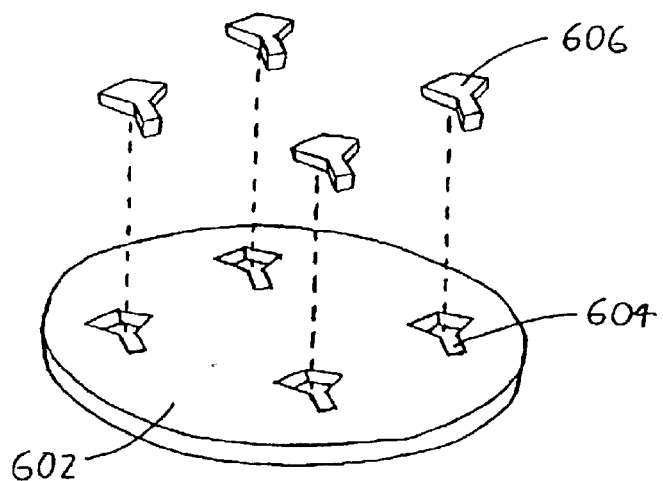
FIG. 6 is a top perspective view of a second study object 602 similar to that of FIG. 4, but wherein study specimens 606 are placed both on and within the second study object 602.

A fourth preferred version of the invention (illustrated in FIG. 6) follows most of the steps of the second version discussed above, but here the second study object 602 is formed with (or has formed therein) recesses 604 which have shapes complementary to those of the study specimens 606. The recesses 604 are preferably formed by etching, milling, or other processes at nonfunctional blank or "dead" locations on the second study object 602 so that they do not interfere with the functionality of the second study object 602. The recesses 604 preferably have a depth such that the study specimens 606, when inserted therein, rest flush with (or very close to flush with) the surface(s) of the second study object 602 whereupon the recesses 604 are formed. After insertion of study specimens 606 within the recesses 604 (and after affixing the study specimens 606 therein, if desired), surface polishing may be used so that the exposed surface(s) of the study specimens 606 are effectively coplanar with the exposed surface(s) of the second study object 602. Thus, when the study specimens 606 rest upon and within the second study object 602, they are more likely to obtain the same treatment as the second study object 602 during layer deposition processes since they will rest in at least substantially the same plane. This version of the invention accounts for the possibility in the second version of the invention that the study specimens may receive different treatment because their surfaces that receive deposited layers may rest in a different plane than the surfaces of the second study object that receive deposited layers. This version of the invention is therefore useful where the processing methods to which the second study object 602 is subjected require uniform deposition of fluids, e.g., spin casting and certain photolithographic processes, and wherein study specimens 606 which present a top surface which is not coplanar with the second study object 602 might not accurately represent the treatment of the second study object 602 during processing. For other fabrication processes such as epitaxial thin film deposition and ion implantation, study specimens 606 which are several microns thick, and which are not coplanar with the second study object 602 (as in the second version of the invention), should reflect little or no appreciable difference in processing treatment and should therefore present a generally accurate depiction of the second study object 602.

Figure 7:
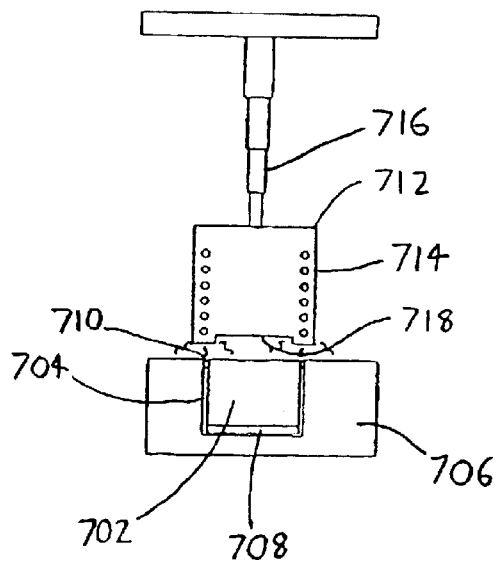
FIGS. 7 and 8 illustrate a side elevational view of a manipulator 714 useful for placing study specimens 702 within a second study object 706 (as illustrated in FIG. 6) and removing them therefrom.
Figure 8:
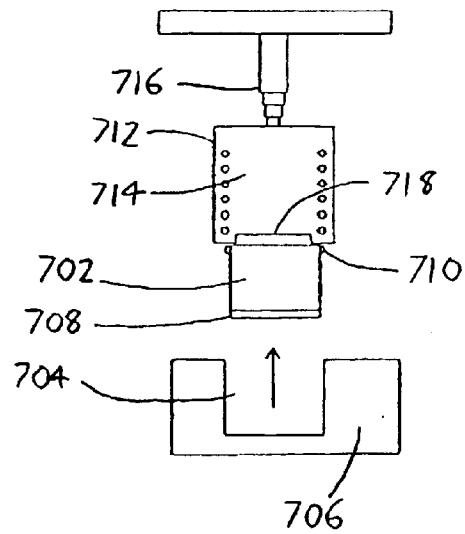

An arrangement which can be used to speed placement of the study specimens in the fourth version of the invention is illustrated in FIGS. 7 and 8. Here, a study specimen 702 similar to the study specimens 606 is shown inserted within a recess 704 formed in a second study object 706. The first study object (not shown) from which the study specimen 702 is formed has a magnetically susceptible layer 708 provided thereon so that the study specimen 702 may be more easily manipulated with the application of magnetic force. Such a layer 708, if not provided on the first study object, can be deposited on a surface of the first study object using standard deposition processes. Rather than placing the study specimen 702 within the recess 704 of the second study object 706 with a friction fit, the study specimen 702 is affixed therein by a bonding agent 710 which allows reversible bonding and removal by application of heat (e.g., an alloy such as indalloy or a low melting temperature polymeric adhesive). An automated robotic device 712 having a manipulator 714 and a movable arm 716 is also shown wherein the manipulator 714 has an electromagnet therein, and also preferably some form of an emitter capable of activating the bonding agent 710. To remove the study specimen 702 from the second study object 706 for analysis, the manipulator 714 is moved above the study specimen 702 within the second study object 706, and the magnetically susceptible layer 708 may be used to precisely position the location of the manipulator 714 via a force feedback mechanism from its electromagnet. To remove the study specimen 702, the manipulator 714 applies an appropriate activation energy to cause the study specimen 702 to be loosened from the recess 704, whereupon the electromagnet of the manipulator 714 then withdraws the study specimen 702 and holds it to the manipulator 714 for transport. Depending upon how the study specimen 702 is bonded within its recess 704, the manipulator 714 could apply heat (as by infrared illumination) to melt a solder or polymer, apply ultraviolet light to degrade a polymer or other adhesive, or apply another form of activation energy to the bonding agent 710. If the study specimen 702 is frictionally fit within the recess 704, applied magnetic force from the manipulator 714 may be sufficient in itself to remove the study specimen 702. Preferably, the face of the manipulator 714 which meets the study specimen 702 has a recess 718 formed therein in order to help prevent damage to the processed surface of the study specimen 702. The arm 716 is then retracted to pull the study specimen 702 away from the second study object 706, and can be used to transport the study specimen 702 for subsequent microanalysis.

As previously noted, where study specimens are to be analyzed by use of an atom probe (the preferred form of microanalyzer for use with the invention), it is useful to form raised study regions in the study specimens prior to microanalysis. While such study regions are often formed by FIB milling processes, they can also be fabricated by a number of photolithographic and surface roughening methods known in the art. Such study regions may be formed prior to, during, or after the various steps described above; for example, the study regions may be formed in the study specimens prior to their removal from the first study object, or may instead be formed immediately prior to microanalysis. It was previously noted that where certain types of layer deposition processes are used (such as spin casting), it is helpful to have the exposed surfaces of the study specimen rest flush with the exposed surfaces of the second study object so that discontinuities in the exposed surfaces will not alter the morphology of the deposited layers. In similar fashion, where these "sensitive" layer deposition processes are used, it may be less useful to form study regions in the study specimens prior to layer deposition since the discontinuous surfaces of the study regions might also affect the layer morphology. If a study specimen bearing pre-formed study regions is subjected to a layer deposition process which is sensitive to the discontinuous surfaces surrounding the study regions, the study specimen will still be usable for microanalysis since the central axes of any protrusions in the study regions will be minimally affected by layer deposition irregularities. However, any adjacent sloping or significantly depressed areas of the study regions may have such significantly different morphology that they will not accurately represent the layers deposited on the second study object, and therefore preformed study regions, while allowing easier processing of study specimens, may result in a study specimen yielding less useful information. A method is therefore illustrated in FIG. 9 wherein any preformed study regions in a study specimen may effectively be hidden during deposition processes so that such study regions will not distort the results of such processes during later microanalysis.

Figure 9:
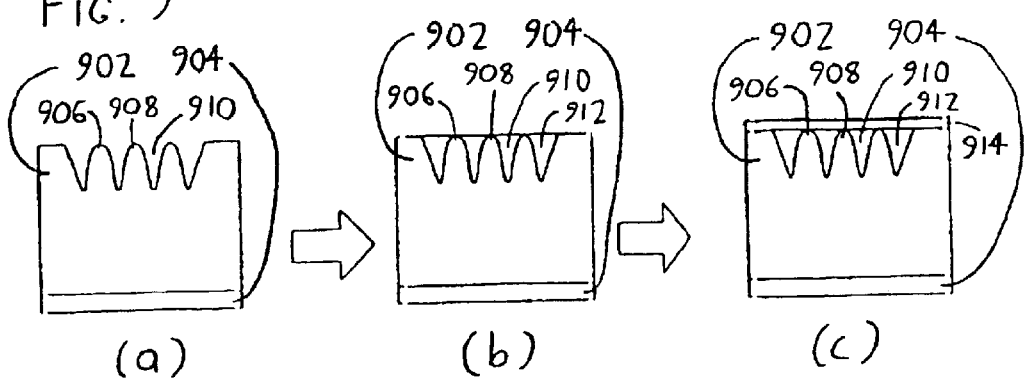
FIG. 9 illustrates, in views (a)–(e), exemplary steps for processing a study specimen 902 having a predefined study region 906 having protrusions 908 suitable for microanalysis by an atom probe.
Figure 9:
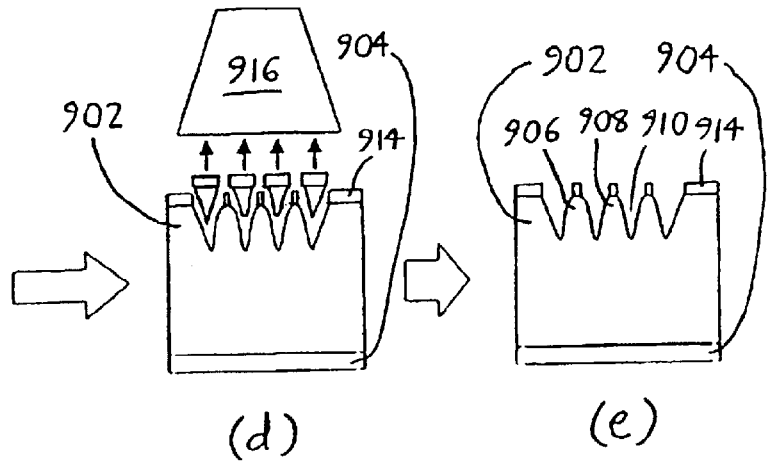

Referring to FIG. 9 at (a), a study specimen 902 (with magnetically susceptible layer 904) is shown with a top study region 906 including several preformed protrusions 908 suitable for analysis in an atom probe. It is desirable to subject the study region 906 to a manufacturing process, e.g., a layer deposition process, wherein the protrusions 908 will accurately reflect the results of the layer deposition process. As noted above, if a sensitive deposition process is used, the protrusions 908 may only provide an accurate representation of the process near their central axes unless steps are taken to remedy the effects that the spaces 910 between the protrusions 908 have on the sensitive deposition process.

In FIG. 9 at (b), the spaces 910 between the protrusions 908 are filled in with a filler material 912 to provide a uniform planar top surface on the study specimen 902. The filler material 912 is a sacrificial layer which will be removed after the study specimen 902 is subjected to the layer deposition process, and it may be formed of polymers, solders, evaporated metals, or other materials. The filler material 912 may itself include multiple layers. For example, the base layer of the filler material 912 could be formed of a material which does not strongly adhere to the study specimen 902, and subsequent layers may then be chosen to facilitate the removal of the entirety of the sacrificial filler material 912; for example, evaporated nickel could allow later magnetic removal of the filler material 912. Alternatively, certain polymers or alloys could be chosen for combination as filler material 912, and for ready removal by a combination of irradiation or heating combined with suction, or by application of ultrasonic energy.

In FIG. 9 at (c), the study specimen 902 is subjected to a layer deposition process, resulting in layer 914 resting atop the study specimen 902 and filler material 912.

In FIG. 9 at (d), the filler material 912 is destroyed and/or removed along with corresponding portions of the deposited layer 914; for example, the removal mechanism 916 might be a suction device which serves to pull filler material 912 having low bonding strength from the study specimen 902, or a magnetic device which serves to pull magnetic filler material 912 from the study specimen 902. Since the deposited layer(s) 914 resting atop the filler material 912 are very thin and adhere to the filler material 912 to a greater extent than they adhere to surrounding portions of the deposited layer(s) 914, they will be removed along with their underlying filler material 912.

It is understood that the various preferred embodiments are shown and described above to illustrate different possible features of the invention and the varying ways in which these features may be combined. For example, it was described above which aspects of the first and second preferred versions of the invention were interchangeable, and which aspects of the second and third preferred versions of the invention were interchangeable. It should therefore be apparent in accordance with the teachings set forth herein that other aspects of the various versions of the invention are also interchangeable. To illustrate, the study specimens 102 in the first version of the invention (and as shown in FIG. 1) could be configured similarly to the study specimens 302 in the second version of the invention (and as shown in FIG. 3), and the specimen holder/second study object 202 of FIG. 2 could be configured similarly to the second study object 602 of FIG. 6. Thus, referring to FIG. 6, the first version of the invention would utilize study specimens 606 received and microanalyzed within the second study object 602. As another illustration, the robot 712 of FIG. 1 could be used in conjunction with the study specimens 208 of FIG. 2. In similar fashion, numerous other combinations are regarded as being within the scope of the invention.

Apart from combining the different features of the above embodiments in varying ways, other modifications are also considered to be within the scope of the invention. Following is an exemplary list of such modifications.

First, if desired, prior to milling, etching, or otherwise forming study specimens, recesses in study objects, etc., the operator may apply a protective layer to the study object and/or the area of the study specimen, as discussed by U.S. Pat. Nos. 6,140,652, 6,188,068, 6,194,720, and others.

Second, apart from the pincer-like micromanipulator 110 illustrated in phantom in FIG. 1 and the electrostatic and magnetic micromanipulators previously mentioned, numerous other types of micromanipulators can be used in the practice of the invention. For example, attraction and repulsion of study specimens could also occur by gas pressure (i.e., the application of vacuum and/or pressurized gas). It is noted that while micromanipulators such as the micromanipulator 110 are often actuated by piezoelectric elements, direct manipulation by piezoelectric elements, as by inserting a piezoelectric element into an aperture in a study specimen and expanding and contracting the element to grasp and release it, is also possible.

Third, other means of affixing the study specimens to the second study object apart from electrostatic attraction, magnetic attraction, chemical and/or mechanical adhesion, friction fitting, etc. are possible. Another example of a useful reversible form of affixment is to form a protrusion on a portion of a study specimen, and form a receiving recess within the second study object, whereby a mechanical (and more then merely frictional) fit between the specimen and object is achieved. For example, a study specimen may bear a protrusion having an irregular cross-section defined about an axis of rotation, and a study object may have a recess which may receive the protrusion in lock-and-key fashion, such that insertion of the protrusion within the recess and rotation therein will prevent withdrawal of the protrusion along its axis of rotation.

Fourth, while it was previously noted that the second study object may be marked for easier identification of study specimens situated thereon (as with the markings shown adjacent the recesses 206 in FIG. 2), it is also possible to provide such markings on a study specimen itself. It is noted that markings need not be alphanumeric characters, and could instead be bar codes or other encoded/patterned markings, fluorescent markers, and/or any other features allowing unique identification of study specimens and/or their locations on study objects.

Fifth, while the portions of the foregoing discussion dealing with the definition of study regions focused on study regions having protrusions well-suited for atom probe analysis, it is noted that study regions suitable for microanalysis by one or more other forms of microanalyzers are also feasible. As an example, apart from raised protrusions, study regions might instead (or additionally) bear elongated slabs or other shapes useful for TEM analysis. Study regions having shaped surfaces useful for analysis by several different types of microanalyzers are also possible, e.g., a protrusion-bearing slab or wedge formed for both atom probe and TEM analysis.

Sixth, while most of the foregoing examples assumed that inorganic materials such as silicon would be used for study specimens and/or study objects, the invention may accommodate use of organic materials as well. Biological and organic materials may require special processing to maintain structure during specimen preparation due to the lability of such materials. For example, some materials may be in a frozen hydrated state at all stages of preparation in vacuum, for example, during FIB treatment and atom probe microanalysis. Alternatively, biological and organic materials may require chemical fixation, dehydration, and drying by means known in the art to prepare them for scanning electron microscopy. Since organic and dried biological materials have very low electrical conductivity, this may require coating the specimen with carbon or evaporated metals prior to FIB etching to create the proper geometry for imaging.

Preferred embodiments of the invention have been described above in order to illustrate how to make and use the invention. The invention is not intended to be limited to these embodiments, but rather is intended to be limited only by the claims set out below. Thus, the invention encompasses all alternate embodiments that fall literally or equivalently within the scope of these claims.

What is claimed is:

1. A method of preparing a specimen for atom probe microanalysis comprising:
   a. forming one or more regions on an object, the regions being suitable for atom probe microanalysis;
   b. subjecting one or more of the regions to a manufacturing process wherein zones of different materials are defined on the regions; and
   c. thereafter microanalyzing at least one of the processed regions with an atom probe.

2. The method of claim 1 wherein the manufacturing process is a layer deposition process.

3. The method of claim 1 wherein the manufacturing process is chosen from at least one of spin casting, photolithography, epitaxial thin film deposition, and ion implantation.

4. The method of claim 1 wherein the regions are separated from the object prior to the step of microanalysis.

5. The method of claim 4 wherein the separated regions are situated on or within a second object prior to the step of microanalysis.

6. The method of claim 1 wherein the regions are separated from the object after the step of defining zones of different materials on the regions.

7. The method of claim 1 wherein the step of forming regions on the object includes forming one or more protrusions on each region.

8. The method of claim 7 wherein the protrusions are formed by removing material from the object about the boundaries of each protrusion.

9. The method of claim 1 wherein the object is a semiconductor wafer.

10. The method of claim 1 wherein the object contains an integrated circuit.

11. The method of claim 10 wherein at least one of the regions is situated adjacent to the integrated circuit.

12. A method of preparing a specimen for atom probe microanalysis comprising:
   a. defining a region suitable for atom probe microanalysis on an object;
   b. depositing material on the region; and
   c. thereafter microanalyzing the region with an atom probe.

13. The method of claim 12 wherein the step of defining the region includes forming a protrusion on the object.

14. The method of claim 13 wherein the step of forming the protrusion on the object includes removing material from the object to leave the protrusion remaining.

15. The method of claim 12 wherein the object is a semiconductor wafer.

16. The method of claim 12 wherein the object contains an integrated circuit.

17. The method of claim 16 wherein at least one of the regions is situated adjacent to the integrated circuit.

18. The method of claim 12 wherein the region is separated from the object prior to material deposition.

19. The method of claim 12 wherein the region is separated from the object prior to microanalysis.

20. The method of claim 19 wherein the region is separated from the object after material deposition.

21. The method of claim 19 wherein:
   a. the separated region is placed on or within a second object, and
   b. material is then deposited onto the second object and separated region together.

22. The method of claim 19 wherein:
   a. the separated region is placed on or within a second object, and
   b. the second object and the separated region are then microanalyzed together.

23. A method of preparing a specimen for atom probe microanalysis comprising:
   a. defining one or more regions on an object, each region containing one or more protrusions suitable for atom probe microanalysis;
   b. depositing material on at least one of the regions; and
   c. thereafter microanalyzing at least one of the regions with an atom probe.

* * * * *